(12) United States Patent
Baker

(10) Patent No.: US 8,357,090 B2
(45) Date of Patent: Jan. 22, 2013

(54) METHOD AND APPARATUS FOR ESTIMATING WATER RESERVES

(75) Inventor: Clark R. Baker, Newman, CA (US)

(73) Assignee: Covidien LP, Mansfield, MA (US)

( * ) Notice: Subject to any disclaimer, the term of this patent is extended or adjusted under 35 U.S.C. 154(b) by 1452 days.

(21) Appl. No.: 11/716,778

(22) Filed: Mar. 9, 2007

(65) Prior Publication Data

US 2008/0221406 A1  Sep. 11, 2008

(51) Int. Cl.
*A61B 5/00* (2006.01)

(52) U.S. Cl. ........................................... 600/306

(58) Field of Classification Search .............. 600/306
See application file for complete search history.

(56) References Cited

U.S. PATENT DOCUMENTS

| | | |
|---|---|---|
| 3,998,550 A | 12/1976 | Konishi et al. |
| 4,066,068 A | 1/1978 | Nilsson et al. |
| 4,364,008 A | 12/1982 | Jacques |
| 4,711,244 A | 12/1987 | Kuzara |
| 4,723,554 A | 2/1988 | Oman et al. |
| 4,805,623 A | 2/1989 | Jobsis |
| 4,850,365 A | 7/1989 | Rosenthal |
| 4,860,753 A | 8/1989 | Amerena |
| 4,883,055 A | 11/1989 | Merrick |
| 4,907,594 A | 3/1990 | Muz |
| 5,057,695 A | 10/1991 | Hirao et al. |
| 5,086,781 A | 2/1992 | Bookspan |
| 5,111,817 A | 5/1992 | Clark et al. |
| 5,146,091 A | 9/1992 | Knudson |
| 5,224,478 A | 7/1993 | Sakai et al. |
| 5,277,181 A | 1/1994 | Mendelson et al. |
| 5,279,295 A | 1/1994 | Martens et al. |
| 5,282,467 A | 2/1994 | Piantadosi et al. |
| 5,337,745 A | 8/1994 | Benaron |
| 5,337,937 A | 8/1994 | Remiszewski et al. |
| 5,348,004 A | 9/1994 | Hollub |
| 5,355,880 A | 10/1994 | Thomas et al. |
| 5,377,674 A | 1/1995 | Kuestner |
| 5,499,627 A | 3/1996 | Steuer et al. |
| 5,615,689 A | 4/1997 | Kotler |
| 5,687,721 A | 11/1997 | Kuhls |
| 5,701,902 A | 12/1997 | Vari et al. |
| 5,720,284 A | 2/1998 | Aoyagi et al. |
| 5,735,284 A | 4/1998 | Tsoglin et al. |
| 5,747,789 A | 5/1998 | Godik |

(Continued)

FOREIGN PATENT DOCUMENTS

EP  1184663 A2  3/2002

(Continued)

OTHER PUBLICATIONS

U.S. Appl. No. 11/528,154, filed Sep. 27, 2006, Debreczeny et al.

(Continued)

*Primary Examiner* — Max Hindenburg
*Assistant Examiner* — Renee Danega
(74) *Attorney, Agent, or Firm* — Fletcher Yoder

(57) ABSTRACT

A system and method are provided for a water reserve index. The method includes determining a lean water fraction of tissue for at least one tissue site and determining skin thickness for the at least one tissue site. The lean water fraction and skin thickness are combined to produce a water reserve estimate.

9 Claims, 4 Drawing Sheets

U.S. PATENT DOCUMENTS

| | | | |
|---|---|---|---|
| 5,755,672 A | 5/1998 | Arai et al. |
| 5,788,643 A | 8/1998 | Feldman |
| 5,803,908 A | 9/1998 | Steuer et al. |
| 5,827,181 A | 10/1998 | Dias et al. |
| 5,833,602 A | 11/1998 | Osemwota |
| 5,853,364 A | 12/1998 | Baker, Jr. et al. |
| 5,860,919 A | 1/1999 | Kiani-Azarbayjany et al. |
| 5,906,582 A | 5/1999 | Kondo et al. |
| 6,064,898 A | 5/2000 | Aldrich |
| 6,125,297 A | 9/2000 | Siconolfi |
| 6,149,591 A | 11/2000 | Henderson et al. |
| 6,178,342 B1 | 1/2001 | Thompson et al. |
| 6,222,189 B1 | 4/2001 | Misner et al. |
| 6,246,894 B1 | 6/2001 | Steuer et al. |
| 6,280,396 B1 | 8/2001 | Clark et al. |
| 6,336,044 B1 | 1/2002 | Ghiassi et al. |
| 6,370,426 B1 | 4/2002 | Campbell et al. |
| 6,400,971 B1 | 6/2002 | Finarov et al. |
| 6,402,690 B1 | 6/2002 | Rhee et al. |
| 6,442,408 B1 | 8/2002 | Wenzel et al. |
| 6,466,807 B1 | 10/2002 | Dobson et al. |
| 6,488,677 B1 | 12/2002 | Bowman et al. |
| 6,512,936 B1 | 1/2003 | Monfre et al. |
| 6,591,122 B2 | 7/2003 | Schmitt |
| 6,592,574 B1 | 7/2003 | Shimmick et al. |
| 6,600,946 B1 | 7/2003 | Rice |
| 6,606,509 B2 | 8/2003 | Schmitt |
| 6,615,064 B1 | 9/2003 | Aldrich |
| 6,635,491 B1 | 10/2003 | Khalil et al. |
| 6,636,759 B2 | 10/2003 | Robinson |
| 6,643,543 B2 | 11/2003 | Takehara et al. |
| 6,654,620 B2 | 11/2003 | Wu et al. |
| 6,668,181 B2 | 12/2003 | Wenzel et al. |
| 6,675,029 B2 | 1/2004 | Monfre et al. |
| 6,687,519 B2 | 2/2004 | Steuer et al. |
| 6,777,240 B2 | 8/2004 | Hazen et al. |
| 6,849,046 B1 | 2/2005 | Eyal-Bickels |
| 6,873,865 B2 | 3/2005 | Steuer et al. |
| 6,950,699 B1 | 9/2005 | Manwaring et al. |
| 6,961,598 B2 | 11/2005 | Diab |
| 7,211,043 B2 * | 5/2007 | Pruche et al. ............... 600/306 |
| 7,277,741 B2 | 10/2007 | Debreczeny et al. |
| 7,283,242 B2 | 10/2007 | Thornton |
| 7,343,186 B2 | 3/2008 | Lamego et al. |
| 2001/0020122 A1 | 9/2001 | Steuer et al. |
| 2003/0060692 A1 | 3/2003 | Ruchti et al. |
| 2003/0060693 A1 | 3/2003 | Monfre et al. |
| 2003/0220548 A1 | 11/2003 | Schmitt |
| 2004/0127777 A1 | 7/2004 | Richti et al. |
| 2004/0147034 A1 | 7/2004 | Gore et al. |
| 2004/0230106 A1 * | 11/2004 | Schmitt et al. ............... 600/310 |
| 2005/0203357 A1 | 9/2005 | Debreczeny et al. |
| 2005/0267346 A1 | 12/2005 | Faber et al. |
| 2006/0020181 A1 | 1/2006 | Schmitt |
| 2006/0052680 A1 | 3/2006 | Diab |
| 2006/0084864 A1 | 4/2006 | Schmitt et al. |
| 2006/0167350 A1 | 7/2006 | Monfre et al. |
| 2006/0253016 A1 | 11/2006 | Baker, Jr. et al. |
| 2006/0276696 A1 | 12/2006 | Schurman |
| 2007/0032707 A1 | 2/2007 | Coakley et al. |
| 2007/0032709 A1 | 2/2007 | Coakley et al. |
| 2007/0032710 A1 | 2/2007 | Raridan et al. |
| 2007/0032711 A1 | 2/2007 | Coakley et al. |
| 2007/0032712 A1 | 2/2007 | Raridan et al. |
| 2007/0032713 A1 | 2/2007 | Eghbal et al. |
| 2007/0032716 A1 | 2/2007 | Raridan et al. |
| 2007/0073122 A1 | 3/2007 | Hoarau |
| 2007/0073123 A1 | 3/2007 | Raridan, Jr. et al. |
| 2007/0073125 A1 | 3/2007 | Hoarau et al. |
| 2007/0073126 A1 | 3/2007 | Raridan, Jr. |
| 2007/0073128 A1 | 3/2007 | Hoarau et al. |
| 2007/0078309 A1 | 4/2007 | Matlock |
| 2007/0078311 A1 | 4/2007 | Al-Ali et al. |
| 2007/0260129 A1 | 11/2007 | Chin |
| 2007/0260130 A1 | 11/2007 | Chin |
| 2007/0260131 A1 | 11/2007 | Chin |
| 2007/0282178 A1 | 12/2007 | Scholler et al. |
| 2007/0282183 A1 | 12/2007 | Scholler et al. |
| 2008/0004513 A1 | 1/2008 | Walker et al. |
| 2008/0058622 A1 | 3/2008 | Baker |
| 2008/0076980 A1 | 3/2008 | Hoarau |
| 2008/0076981 A1 | 3/2008 | Hoarau |
| 2008/0076994 A1 | 3/2008 | Hoarau |
| 2008/0076995 A1 | 3/2008 | Hoarau |
| 2008/0076996 A1 | 3/2008 | Hoarau |
| 2008/0154104 A1 | 6/2008 | Lamego et al. |

FOREIGN PATENT DOCUMENTS

| | | |
|---|---|---|
| FR | 2710517 | 4/1995 |
| JP | 4-40940 | 2/1992 |
| JP | 05-329163 | 12/1993 |
| JP | 11-244266 | 9/1999 |
| JP | 2004 081427 A | 3/2004 |
| JP | 26075354 | 3/2005 |
| JP | 25169020 | 6/2005 |
| JP | 25278758 | 10/2005 |
| WO | WO 95/19562 A | 7/1995 |
| WO | WO 98/34097 | 8/1998 |
| WO | WO 00/71025 A1 | 11/2000 |
| WO | WO 93/13706 A2 | 1/2001 |
| WO | WO 01/16577 A1 | 3/2001 |
| WO | WO 0150948 A1 | 7/2001 |
| WO | WO 0195800 A1 | 12/2001 |
| WO | WO 03/010510 A | 2/2003 |
| WO | WO 2005/041765 A | 5/2005 |

OTHER PUBLICATIONS

U.S. Appl. No. 11/528,218, filed Sep. 27, 2006, Campbell et al.

U.S. Appl. No. 11/529,024, filed Sep. 28, 2006, Agashe et al.

U.S. Appl. No. 11/541,010, filed Sep. 29, 2006, Baker, Jr. et al.

Buijs, K., et al., "Near-Infrared Studies of the Structure of Water. I. Pure Water," *The Journal of Chemical Physics*, vol. 39, No. 8, pp. 2035-2041 (Oct. 15, 1963).

Martens, H., et al., "Unscrambling Multivariate Data from Mixtures: I: Fat, water and protein determination in meat by near-infrared reflectance spectroscopy, II: soy protein and collagen determination in meat products from amino acid data," *Meat Res. Workers, Proc. European Meeting*, pp. 146-149 (1980).

Wolfgang, Arneth, "Multivariate Infrared and near-infrared Spectroscopy: rapid analysis of protein, fat and water in meat," *Food Res and Data Analysis, Proc from IUoST Symp*, Oslo, Norway, pp. 239-251 (1983).

Potts, R.O., et al., "A Noninvasive, in Vivo Technique to Quantitatively measure Water Concentration of the Stratum Corneum Using Attenuated Total-Reflectance Infrared Spectroscopy," *Arch. Dermatol Res.*, vol. 277, pp. 489-495 (1985).

Valdes, E. V., et al., "Determination of Crude Protein and Fat in Carcass and Breast Muscle Samples of Poultry by Near Infrared Reflectance Spectroscopy," *Poultry Science*, vol. 65, pp. 485-490 (1986).

Bommannan, D., et al., "Examination of Stratum Corneum Barrier Function in Vivo by Infrared Spectroscopy," *J. Invest Dermatol*, vol. 95, pp. 403-408 (1990).

Edwardson, P. et al., "The Use of FT-IR for the Determination of Stratum Corneum Hydration in Vitro and in Vivo," *J. of Pharmaceutical & Biomed. Analysis*, vol. 9, Nos. 10-12, pp. 1089-1094, 1991.

Horber, F.F., et al., "Impact of hydration status on body composition as measured by dual energy X-ray absorptiometry in normal volunteers and patients on haemodialysis," *The British Journal of Radiology*, vol. 65, pp. 895-900 (1992).

Schmitt et al., *Proc. SPIE*, "Measurement of blood hematocrit by dual-wavelength near-IP photoplethysmography," 1641:150-161 (1992).

Martin, K., "Direct Measurement of Moisture in Skin by NIR spectroscopy," *J. Soc. Cosmet. Chem.*, 44:249-261 (1993).

Matcher, S. J., et al., "Absolute quantification of deoxyhaemoglobin concentration in tissue near infrared spectroscopy," *Phys. Med. Biol.*, vol. 39, pp. 1295-1312 (1994).

Takeo, T. et al., "Skin Hydration State Estimation Using a Fiber-Optic Refractometer," *Applied Optics*, vol. 33, No. 19, Jul. 1994, p. 4267-72.

Isaksson, Tomas, et al., "Non-Destructive Determination of Fat, Moisture and Protein in Salmon Fillets by Use of Near-Infrared Diffuse Spectroscopy," *J. Sci Food Agric.*, vol. 69, pp. 95-100 (1995).

Kumar, Gitesh, et al., "Non-Invasive Optical Assessment of Tissue Hydration," *International conference on Biomedical Engineering*, Jun. 3-5, 1996, Hong Kong, pp. C2-C5.

Schmitt et al., *Proc. SPIE*, "Optimum wavelengths for measurement of blood hemoglobin content and tissue hydration by NIR spectrophotometry," 2678:442-453 (1996).

Martin, Kathleen, "In Vivo Measurements of Water in Skin by Near-Infrared Reflectance," *Applied Spectroscopy*, vol. 52, No. 7, 1998, pp. 1001-1007.

Stranc, M.F., et al., "Assessment of tissue viability using near-infrared spectroscopy," *British Journal of Plastic Surgery*, vol. 51, pp. 210-217, (1998).

Wilhelm, K.P., "Possible Pitfalls in Hydration Measurements," *Skin Bioengineering Techniques and Applications in Dermatology and Cosmetology*, vol. 26, pp. 223-234 (1998).

Fornetti, Willa C., et al., "Reliability and validity of body composition measures in female athletes," Journal of Applied Physiology, vol. 87, pp. 1114-1122, (1999).

Kalantar-Zadeh, Kamyar, et al., "Near infra-red interactance for nutritional assessment of dialysis patients," *Nephrol Dial Transplant*, vol. 14, pp. 169-175 (1999).

Sowa et al., "Near-infrared spectroscopic assessment of tissue hydration following surgery", *Journal of Surgical Research*, 86:62-69 (1999).

Lucassen, G., et al., "Water Content and Water Profiles in Skin Measured by FTIR and Raman Spectroscopy," *Proc. SPIE*, vol. 4162, pp. 39-45 (2000).

Attas, Michael, et al., "Visualization of cutaneous hemoglobin oxygenation and skin hydration using near-infrared spectroscopic imaging," *Skin Research and Technology*, vol. 7, pp. 238-245, (2001).

Du, Y., et al., "Optical properties of porcine skin dermis between 900 nm and 1500 nm," *Phys. Med. Biol.*, vol. 46, pp. 167-181 (2001).

Kalantar-Zadeh, Kamyar, et al., "Near infra-red interactactance for Longitudinal Assessment of Nutrition in Dialysis Patients," *Journal of Renal Nutrition*, vol. 11, No. 1, pp. 23-31 (Jan. 2001).

Lever, M., et al., "Some ways of looking at compensatory kosmotropes and different water environments," *Comparative Biochemistry and Physiolog.*, vol. 130, Part A, pp. 471-486, (2001).

Sowa et al., "Near infrared spectroscopic assessment of hemodynamic changes in the early post-burn period," *Burns*, 27(3):241-9 (2001).

Troy, Tamara L., et al., "Optical properties of human skin in the near infrared wavelength range of 1000 to 2200nm," *Journal of Biomedical Optics*, vol. 6, No. 2, pp. 167-176 (Apr. 2001).

Attas, E. Michael, et al., "Near-IR Spectroscopic Imaging for Skin Hydration: The Long and the Short of It," *Biopolymers*, vol. 67, No. 2, pp. 96-106 (2002).

Attas, M. et al., "Long-Wavelength Near-Infrared Spectroscopic Imaging for In-Vivo Skin Hydration Measurements," *Vibrational spectroscopy* (Feb. 28, 2002), vol. 28, No. 1, p. 37-43.

Meglinski, Igor V., et al., "Quantitative assessment of skin layers absorption and skin reflectance spectra simulation in the visible and near-infrared spectral regions," *Physiol. Meas.*, vol. 23, pp. 741-753, (2002).

Bouwstra, Joke A., et al., "Water Distribution and Related Morphology in Human Stratum Corneum at Different Hydration Levels," *J. Invest Dermatol*, vol. 150, pp. 750-758 (2003).

Grandjean et al., "Hydration: issues for the $21^{st}$ century", *Nutrition Reviews*, 61(8):261-271 (2003).

Heise, H.M., et al., "Reflectance spectroscopy can quantify cutaneous haemoglobin oxygenation by oxygen uptake from the atmosphere after epidermal barrier distruption," *Skin Research and Technology*, vol. 9, pp. 295-298 (2003).

Kasemsumran, Sumaporn, et al., "Simultaneous determination of human serum albumin, γ-globulin, and glucose in a phosphate buffer solution by near-infrared spectroscopy with moving window partial least-squares regression," *Analyst*, vol. 128, pp. 1471-1477 (2003).

Meglinski, I.V., et al., "Computer simulation of the skin reflectance spectra," *Computer Methods and Programs in Biomedicine*, vol. 70, pp. 179-186, (2003).

Mendelsohn, Richard, et al., "Infrared microspectroscopic imaging maps the spatial distribution of exogenous molecules in skin," *Journal of Biomedical Optics*, vol. 8, No. 2, pp. 185-190 (Apr. 2003).

Merritt, Sean, et al., "Coregistration of diffuse optical spectroscopy and magnetic resonance imaging in a rat tumor model," *Applied Optics*, vol. 42, No. 16, pp. 2951-2959 (Jun. 2003).

Wolf, Martin, et al., "Absolute Frequency-Domain pulse Oximetry of the Brain: Methodology and Measurements," *Oxygen Transport to Tissue XXIV*, Chapter 7, Dunn and Swartz, Kluwer Academic/Plenum Publishers, pp. 61-73 (2003).

J. H. Ali, et al.; "Near Infrared Spectroscopy and Imaging to Prove differences in Water content in normal and Cancer Human Prostate Tissues," *Technology in Cancer Research & Treatment*, vol. 3, No. 5, Oct. 2004; pp. 491-497.

Arimoto et al., "Non-contact skin moisture measurement based on near-infrared spectroscopy", *Applied Spectroscopy*, 58(12):1439-1445 (2004).

Egawa, Mariko et al., "Regional Difference of Water Content in Human Skin Studied by Diffuse-Reflectance Near-Infrared Spectroscopy: Consideration of Measurement Depth," *Applied Spectrometry*, vol. 60, No. 1, 2006.

Martin K, "In Vivo Measurements of Water in Skin by Near-Infrared Reflectance", Applied Spectroscopy, The Society for Applied Spectroscopy, Baltimore, US, vol. 52, No. 7, Jul. 1, 1998.

International Search Report PCT/US2008/003013, 4 pages, mailed Jul. 30, 2008.

\* cited by examiner

METHOD AND APPARATUS FOR ESTIMATING WATER RESERVES

TECHNICAL FIELD

The present invention relates generally to determining physiological parameters and, more particularly, to estimating water reserves.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In healthy individuals, homeostatic control mechanisms ensure that a balance between fluid gain and fluid loss is maintained and, therefore, maintaining fluid balance is typically not an issue requiring attention. In ill individuals, however, the maintenance of body fluid balance may be cause for great concern. Dehydration or edema may occur if fluid balance is not properly maintained. For example, dehydration of infants and children suffering from diarrhea and/or vomiting can be life threatening if not recognized and treated promptly. Additionally, many elderly people have an increased risk of dehydration because they have thin, fragile skin, which is a major reservoir of water for the body.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In accordance with one aspect of the present invention, there is provided a method for determining a water reserve index. The method comprises determining a lean water fraction of tissue and skin thickness for at least one site. The method also comprises combining the lean water fraction and skin thickness to produce a water reserve estimate.

In accordance with another aspect of the present invention, there is provided a method for determining skin thickness. The method comprises emitting electromagnetic radiation from a sensor at an individual's skin and detecting the emitted electromagnetic radiation after it has been scattered and absorbed by constituents of the skin. The method also comprises determining the prominence of spectral features corresponding to a subcutaneous fat layer, wherein the prominence of spectral features indicates skin thickness.

In accordance with yet another aspect of the present invention, there is provided a system for determining a water reserve index. The system includes a sensor comprising an emitter configured to emit near-infrared light and a detector configured to detect the emitted light and generate a signal representative of the detected light. The system also including a monitor communicatively coupled to the sensor and configured to receive the generated signal. The monitor comprising a microprocessor configured to calculate a lean water fraction based on the received signal. The microprocessor further configured to combine the lean water fraction with a skin thickness value to determine a water reserve index. The monitor also comprising a display configured to display the determined water reserve index to the user.

BRIEF DESCRIPTION OF THE DRAWINGS

Certain exemplary embodiments are described in the following detailed description and in reference to the drawings in which.

DETAILED DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with the present technique, a system and method are disclosed for estimating an individual's water reserves. The technique includes determining a water reserve index based on two factors: an estimate of the lean water fraction and the thickness of the skin. The two factors may be used to produce a water reserve index indicative of the amount of water reserves an individual has available in the form of skin cell hydration. The water reserve index may be measured relative to a level of skin hydration clinically determined to be indicative of a dehydrated state. Accordingly, the water reserve index may be indicative of an amount of water above or below the dehydrated level.

Figure 1:
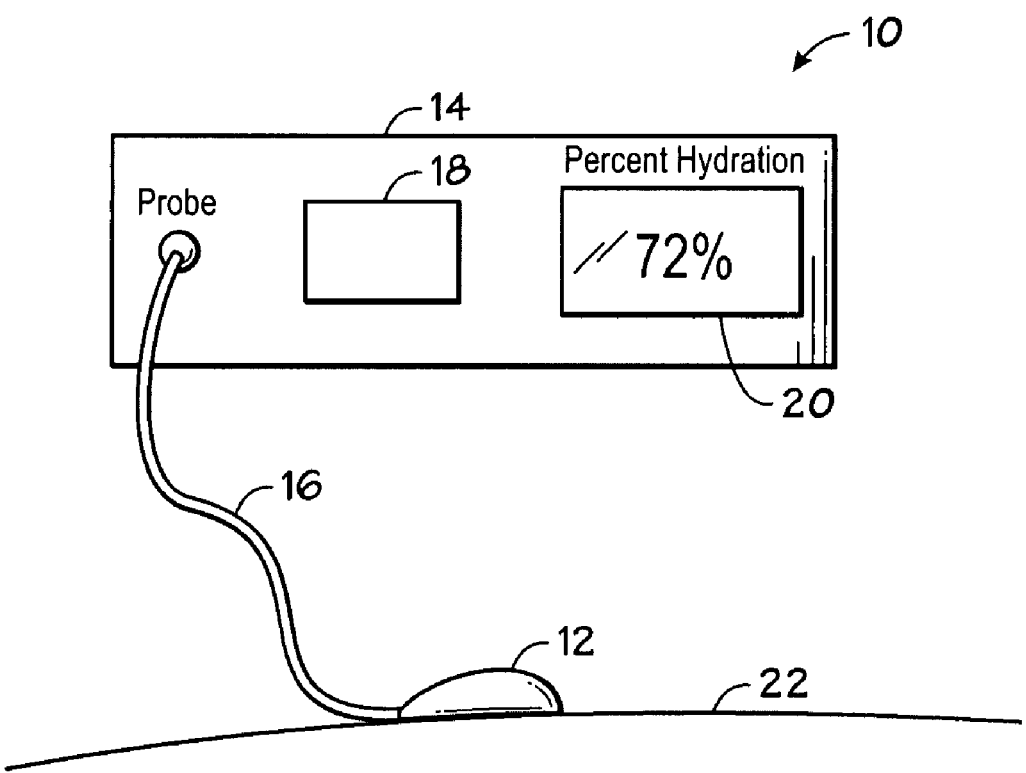
FIG. 1 illustrates a system for determining hydration in accordance with an exemplary embodiment of the present invention.

Turning to FIG. 1, a system for non-invasively determining physiological parameters is illustrated in accordance with an exemplary embodiment of the present invention and is generally designated by the reference numeral 10. The system 10 includes a sensor 12 coupled with a monitor 14 via a cable 16. The system may also include an input device, such as a keyboard 18 and an output device, such as a display 20. The keyboard 18 may be configured to allow a user, such as a clinician, to enter various parameters or baseline hydration levels, as will be discussed below. The display 20 may be configured to display a lean water fraction, a skin thickness, and/or a water reserve index measurement among other things.

Figure 2:
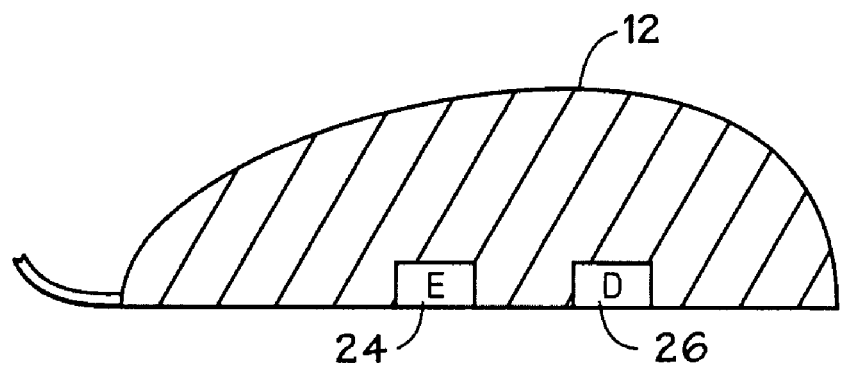
FIG. 2 illustrates a cross-sectional view of a sensor of the system of FIG. 1 in accordance with an exemplary embodiment of the present invention.

The sensor 12 is configured to contact an individual's skin 22 on a site where measurements are to be taken. A cross sectional view of the sensor 12 is shown in FIG. 2 to illustrate that the sensor 12 may include at least one emitter 24 and at least one detector 26 component parts of the sensor 12. As can be seen, the emitter 24 and the detector 26 are located on a substantially flat surface of the sensor 12 so that they may optically couple with an individual's skin 22.

The emitter 24 may include one or more electromagnetic radiation sources or light sources, such as light emitting diodes (LEDs), an array of LEDs, a white light source, a tunable laser, or any other source that transmits electromagnetic radiation within a region of the electromagnetic spectrum useful for the determination of physiological parameters. Specifically, the near-infrared region (NIR) of the electromagnetic spectrum is particularly useful in measuring relative concentrations of tissue constituents for the determination of skin thickness and water content. In the 1100-1400 nm and 1600-1900 nm regions, water, protein and fat have distinctive absorbance spectra that can be used to determine their relative concentrations. As such, the emitter 24 in this embodiment operates in the NIR range.

The detector 26 may be a photosensitive diode, photosensitive transistor or other means for detecting electromagnetic radiation within the range of the electromagnetic spectrum of the emitter 24. The detector 26 is configured to detect electromagnetic radiation originating from the emitter 24 after it has passed through a patient's skin and been absorbed and/or scattered by the constituent parts of the tissue.

The sensor 12 may be a reflection-type sensor, as illustrated in FIG. 1, where the emitter 24 and detector 26 are substantially in the same plane and spaced 1-5 mm apart, or a transmission-type sensor, where the emitter 24 and detector 26 are placed on substantially opposite sides of the tissue site. More specifically, because the detector 26 is in the same plane as the emitter 24 in the reflectance-type sensor, the detector 26 detects light that has been reflected and/or scattered by the tissue. In contrast, in a transmission-type sensor, the sensor's emitter and detector lie in parallel planes on opposing sides of the tissue. The optical path of the light originating from an emitter in a transmission-type sensor is substantially in-line with an imaginary axis connecting the emitter and the detector, and the detector detects light that has been transmitted through the tissue along the optical path.

Methods for estimating the lean water fraction in the skin by near-infrared (NIR) spectrophotometry have been described in the art and a number of theoretical scattering models have been applied to tissue spectra in order to allow for the estimation of constituent spectra. In particular, methods for measuring the lean water fraction in tissue by NIR spectroscopy are described in U.S. Pat. No. 6,591,122, U.S. Pub. No. 2003-0220548, U.S. Pub. No. 2004-0230106, U.S. Pub. No. 2005-0203357, U.S. Pat. App. No. 60/857,045, U.S. patent application Ser. No. 11/283,506, and U.S. patent application Ser. No. 11/282,947, all of which are incorporated herein by reference. In addition to the methods and algorithms disclosed by the above mentioned patents and applications, the spectral absorption bandwidth may be used to estimate tissue constituent concentration and, more specifically, water content of tissue, as disclosed in U.S. patent application Ser. No. 11/528,154 which is also incorporated by reference.

The lean water fraction may generally be described as a ratio of the water-to-protein in the tissue. Protein content may be challenging to estimate because it comprises a class of thousands of different molecules and many of the absorption peaks in the protein spectrum are close to absorption peaks for fat. Water, however, is generally the most prominent absorber in the NIR spectrum. The absorption spectrum of water varies primarily with the degree of hydrogen bonding between water and/or other polar molecules, but most of this variation may be correlated with temperature, which can be easily measured. The lean water fraction may be correlated to a whole body hydration index or a local hydration index.

In addition to an estimate of the lean water fraction in the skin, as determined by the techniques in the incorporated references for example, skin thickness may be used to estimate an individual's water reserves and provide an index of the individual's water reserves. As mentioned above, the skin may be a major reservoir of water for the body. Generally, thicker skin indicates the body has the capacity for storing more water and thinner skin indicates the body has the capacity for storing less water. As will be discussed in greater detail below, the skin thickness may be used in conjunction with other methods for determining hydration levels to estimate an individual's water reserves.

Figure 3:
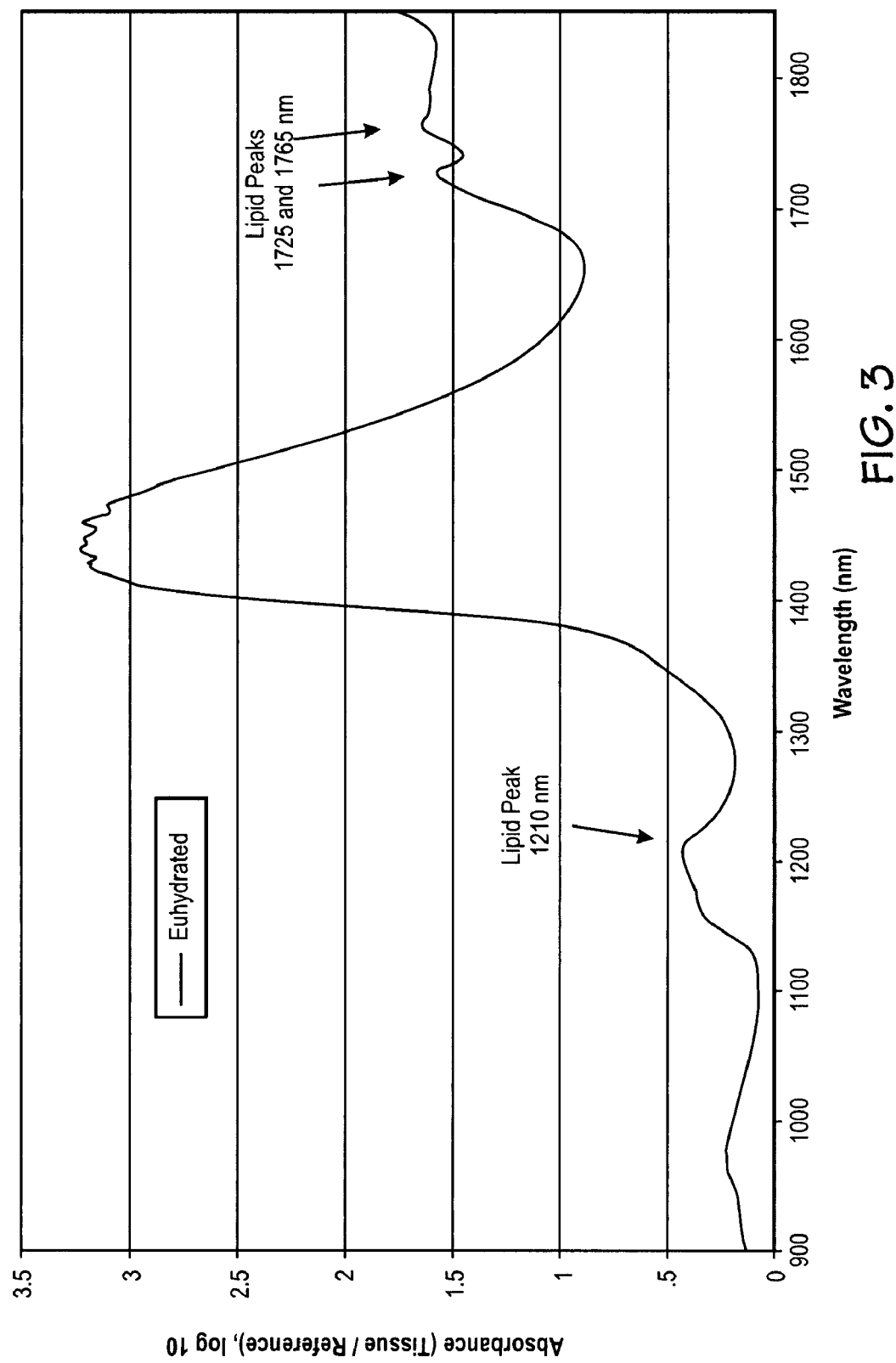
FIG. 3 illustrates a plot of euhydrated skin showing lipid (fat) peaks at 1210 nm, 1725 nm, and 1765 nm.

Skin thickness may be measured by any of a number of suitable techniques. For example, skin thickness may be measured by spectroscopic means. A subcutaneous fat layer can be seen in spectroscopic analysis of the human skin and mammalian skin, in general. As illustrated in FIG. 3, experiments on euhydrated porcine models show that the subcutaneous fat layer is readily visible as lipid peaks at 1210 nm, 1725 nm, and 1765 nm. Sensors configured to have 2.5 mm emitter-detector spacing were using to produce the plots of FIGS. 3 and 4. It is estimated that the mean photon penetration depth is around 1 mm with the 2.5 mm spacing. Based on an evaluation of the plots, fat accounts for about 20-30 percent of the total tissue traversed by near-infrared photons in piglets. It can be estimated that fat will account for a somewhat lower percentage in adult humans.

Figure 4:
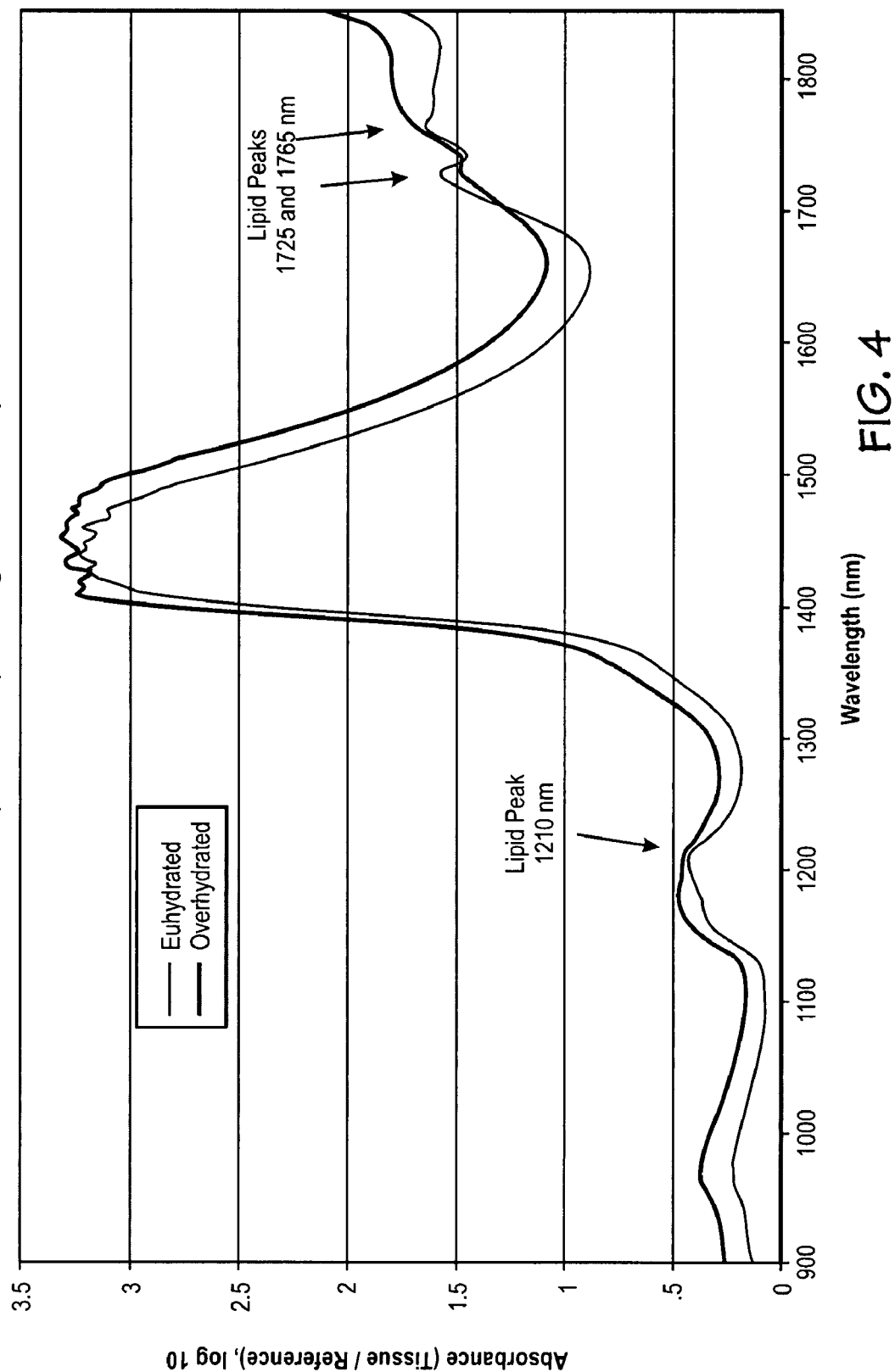
FIG. 4 illustrates a plot of the euhydrated skin of FIG. 3 and plot showing reduction of the lipid peaks as an effect of overhydration.

Turning to FIG. 4, a plot of overhydrated porcine models superimposed on the plot of the euhydrated porcine model of FIG. 3 is illustrated. As can be seen, the lipid peaks are less prominent when the porcine models are in an overhydrated state. The relative amplitude of the lipid peaks is lessened because the skin thickness has increased as more water is stored in the skin in the overhydrated state. The thicker skin results in less of the near-infrared photons traversing the subcutaneous fat layer before being detected. Although not shown in the figures, removal of fluid from the piglets via ultrafiltration causes the fat peaks to become more prominent due to the skin becoming thinner and more of the photons reaching the subcutaneous fat layer. The thickness of the skin, therefore, may be determined based on the amplitude of the fat spectrum relative to the other constituents, protein and water, present in the spectrum.

Specifically, the relative amplitude of the lipid features relative to the rest of the spectrum may be indicative of the water content of the skin. The relative amplitude may be determined by analysis of the full spectrum of a tissue site in comparison to the spectra of pure analytes (water, protein, and fat), as discussed in detail in U.S. Ser. No. 11/716,482 filed Mar. 9, 2007 and titled "Method and Apparatus for Spectroscopic Tissue Analyte Measurement," which is incorporated herein by reference. Alternatively, the relative amplitude of the fat features may be determined using a relatively small number of selected wavelengths, one of which should be absorbed more strongly by fat than water. It has been determined that at least two wavelengths are needed for a reasonable determination of tissue water, so at least three wavelengths may be required to also incorporate an empirical determination of fat relative to water and protein.

Because humans also have a subcutaneous fat layer, the relative amplitude of the lipid features in the NIR skin spectra is useful to determine skin thickness in humans. Although the skin thickness will vary between sites and between individuals, it may be assumed that the subcutaneous fat store is sufficiently thick at most sites to assure that NIR photons will not penetrate below it, and that virtually all the water and protein traversed by the NIR photons will be above the subcutaneous layer. For example, for a healthy adult male weighing 70 kg and having a total surface area of about 18000 $cm^2$, a subcutaneous fat store of 10% of body weight would have a volume of 7800 $cm^3$ and, therefore, average about 4.3 mm thick. Although the subcutaneous fat layer accounts for a lower percentage of the total tissue traversed by the near-infrared photons in humans than in pigs, a correlation between the relative amplitude of the lipid features and skin thickness may be made. As stated above, thinner skin may be indicated by a greater amplitude of the lipid features, including peaks, relative to the other constituents and thicker skin may be indicated by lesser relative amplitude of the lipid features. A correlation factor for correlation between the relative amplitude of lipid features and skin thickness may be empirically determined for specific sites. For example, site specific empirical testing may be performed comparing the relative amplitude of the fat features with water and protein to determine the correlation between the relative amplitude and the skin thickness.

Multiple alternative means for estimating skin thickness are known and may be implemented. For example, Skin thickness may be estimated using high frequency (near 15-20 MHz) ultrasound signals or Harpenden skinfold calipers. The skin thickness estimated by the ultrasound technique may be manually or automatically entered into the system 10, while a skinfold estimate may be manually entered. Because the spectroscopic technique for determining skin thickness is based on the amount of light that penetrates to the subcutaneous fat layer and, in a transmission type sensor, all of the detected light passes through all the tissue layers a transmission type sensor is not adapted to make a skin thickness measurement. Accordingly, one of the above mentioned, techniques for determining skin thickness may be implemented when a transmission type sensor is used.

Figure 5:
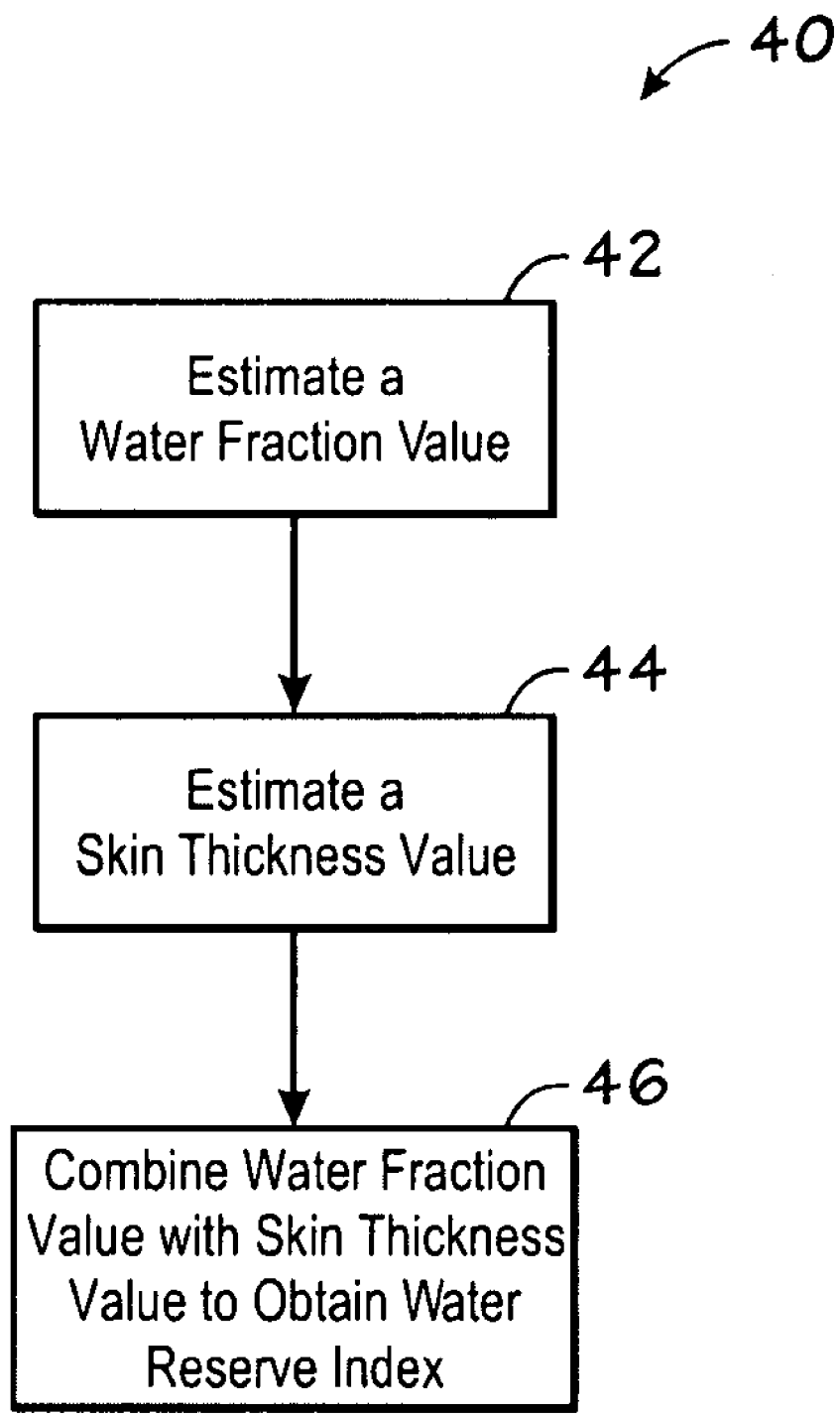
FIG. 5 illustrates a technique for determining a hydration index based on an estimate of the fraction of water in the skin and skin thickness, in accordance with an exemplary embodiment of the present invention.

Once the thickness of the skin is determined, it can be correlated to a hydration level of the individual based on empirically determined relationships between skin thickness and hydration levels. As mentioned above, a water reserve index may be determined based on the combination of two factors indicative of an individual's hydration level. FIG. 5 is a flow chart illustrating a technique 40 for analyzing these two factors to determine a water reserve index. The technique 40 includes estimating a lean water fraction value, as indicated at block 42. The lean water fraction estimation may be performed spectroscopically by one of the above mentioned techniques. For example, in accordance with an exemplary embodiment, the system 10 of FIG. 1 may be configured to determine a lean water fraction in accordance with known algorithms.

Additionally, the technique 40 also includes estimating a skin thickness value, as indicated at block 44. The skin thickness value may be performed in accordance with any one of the above mentioned methods, including spectroscopic, ultrasound, or caliper means. If, for example, the skin thickness is determined spectroscopically, the system 10 may be configured to determine both the lean water fraction value and the skin thickness value in addition to determining the water reserve index, as will be explained below. As described above, if the skin thickness measurement is made spectroscopically, at least three discrete wavelengths may be used, including one at which electromagnetic radiation is absorbed more by fat than by water.

Once the two factors, the lean water fraction value and the skin thickness value, are determined, the system 10 may combine the values to obtain a water reserve index, as indicated at block 46. For example, a water reserve index might be computed using an equation of the form:

$$\text{Water Reserve} = (\text{Lean Water Fraction} - \text{offset}) * \text{Skin\_Thickness},$$

where the offset takes into account that some of the water in the skin is tightly bound to proteins inside or outside of cells and cannot readily move around the body. The computed water reserve index is indicative of the amount of water in the body and may be correlated to a clinically determined dehydrated condition. Specifically, a water reserve index value may be empirically determined for a clinically dehydrated state. The computed water reserve index may use the clinically determined dehydrated water reserve index value as a baseline for determining the amount of water reserves above the dehydrated state.

As mentioned above, skin thickness and hydration values may vary based on the site at which the sensor 12 is taking measurements. To the extent that the normal skin thickness or hydration varies between sites, the proposed hydration index may be site specific. Several means of indicating a skin site are known in the art and may include incorporating an electronic ID chip into sensor design for a specific site. One technique is disclosed in U.S. Ser. No. 11/716,264, filed Mar. 9, 2007 and titled "Method for Identification of Sensor Site by Local Skin Spectrum Data," which is incorporated herein by reference. Additionally, a particular sensor may be designed for use on a particular site, such as the forehead, for example, and it may contain an ID chip indicating that it is taking measurements from that particular site. The monitor 14 (FIG. 1) may also have a keyboard 18, or other input device, through which a user may communicate location detail to the monitor 14. Alternatively, the monitor 14 may provide a display 20 that allows the user to indicate the sensor 12 location. Further, once the monitor 14 knows the location at which measurements are being taken, the monitor 14 may calibrate itself accordingly to increase the accuracy of the system 10. For example, the monitor 14 may be configured to select appropriate coefficients or constants to be used in the algorithms to compensate for any location specific variation in skin thickness and/or hydration. Appropriate coefficients or constants associated with the determination of the lean water fraction, skin thickness, and/or water reserve index may be determined empirically based on clinical studies.

In an alternative embodiment, the monitor 14 may be configured to allow a user, such as a clinician, to input baseline hydration levels for a particular site or, via the keyboard 18. Specifically, for example, a user may enter the clinically determined dehydration values against which the computed water reserve index can be compared to determine if a patient is in a dehydrated or over hydrated state.

Additionally, it is further known that skin thickness increases during the day at sites that typically remain lower than the heart, such as the feet and ankles, as a result of gravitational forces. The skin thickness measurement may, therefore, be adjusted for the elevation of the sensor site relative to the heart. Because the elevation dependent hydration changes occur primarily in the interstitial compartment, the elevation based adjustments may reflect the average elevation differences from the heart over the approximate equilibration time of the interstitial compartment, which may take tens of minutes.

Several techniques that may be implemented for determining the elevation, position and/or orientation of the sensor are discussed in U.S. Pub. No. 20060253016, which is incorporated herein by reference. Specifically, For example, means of determining elevation changes relative to the heart might include settings on the surgical table or hospital bed, a camera, a small tube with fluid and a pressure sensor at one end. In addition, a water probe location sensor may include one or more mechanical linkages, such as, e.g., an arm with a joint, that attaches to a probe. In these cases, the position and/or orientation of a probe may be ascertained from the length of the arm, the angle of its joint, and/or the position of the subject. Remote water probe location sensors may also provide location information relative to the subject's body, such as, e.g., where a sensor uses optical and/or ultrasound emitters (e.g., on the probe, subject, and/or hospital bed) and detectors (e.g., on the sensor). Alternatively, a sensor may include a video camera and/or may use object recognition image processing software to detect probe location and/or tissue site position, orientation, and/or elevation. In yet another example, a sensor may also receive signals from one or more small piezoelectric vibratory gyroscopes located in a probe. These may be the same types of gyroscopes that may be used in automobile navigation systems and may allow detection of probe location information. Other alternative techniques may be implemented and the relative elevation of the sensor may be input to the monitor 14 via the keyboard 18 or the display 20.

Therefore, in computing the skin thickness, the monitor 14 may be configured to use particular coefficients or constants to calibrate for site specific conditions as well as the elevation of the sensor site relative to the heart. As described above, the site specific information and the elevation information may be input manually via the keyboard 18 or monitor 20. Alternatively, the sensor 12 and monitor 14 may be configured to automatically determine the elevation and site specific information.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of tissue hydration, but these techniques may also be utilized for the measurement and/or analysis of other analytes. The invention, therefore, is to cover all modifications, equivalents, and alternatives falling within the spirit and scope of the invention as defined by the following appended claims.

What is claimed is:

1. A system for determining a water reserve index comprising:
    a sensor, the sensor comprising:
        an emitter configured to emit near-infrared light;
        a detector located between 1 to 5 mm from the emitter configured to detect the emitted light and generate a signal representative of the detected light, wherein the emitter and the detector are configured to optically couple with an individual's skin;
    a monitor communicatively coupled to the sensor and configured to receive the generated signal, the monitor comprising:
        a microprocessor configured to calculate a lean water fraction based on the received signal, the microprocessor combining the lean water fraction with a skin thickness value to determine a water reserve index; and
    a display configured to display the determined water reserve index to the user.

2. The system of claim 1 wherein the microprocessor is configured to compute the skin thickness based on the received signal.

3. The system of claim 1 wherein combining the lean water fraction with skin thickness comprises multiplying the lean water fraction with the skin thickness.

4. The system of claim 1 comprising a keyboard configured to allow a user to input parameters pertinent to the determination of a water reserve index.

5. The system of claim 4 wherein the keyboard is configured to allow a user to input sensor location information.

6. The system of claim 4 wherein keyboard is configured to allow a user to input sensor elevation information.

7. The system of claim 1 wherein the display is configured to allow a user to indicate sensor location information.

8. The system of claim 1 wherein the sensor is configured to the monitor location specific information.

9. The system of claim 1 wherein the emitter is 2.5 mm from the detector.

* * * * *